(12) United States Patent
Mogna

(10) Patent No.: US 11,191,792 B2
(45) Date of Patent: Dec. 7, 2021

(54) BACTERIAL COMPOSITION FOR USE IN ATTENUATING THE DECLINE IN PERFORMANCE AFTER EXERCISE

(71) Applicant: Probiotical S.P.A., Novara NO (IT)

(72) Inventor: Giovanni Mogna, Novara (IT)

(73) Assignee: PROBIOTICAL S.P.A., Novara No (IT)

(*) Notice: Subject to any disclaimer, the term of this patent is extended or adjusted under 35 U.S.C. 154(b) by 169 days.

(21) Appl. No.: 15/775,710

(22) PCT Filed: Nov. 17, 2016

(86) PCT No.: PCT/IB2016/056919
§ 371 (c)(1),
(2) Date: May 11, 2018

(87) PCT Pub. No.: WO2017/085656
PCT Pub. Date: May 26, 2017

(65) Prior Publication Data
US 2018/0318363 A1 Nov. 8, 2018

(30) Foreign Application Priority Data
Nov. 19, 2015 (IT) .................. 102015000074653

(51) Int. Cl.
*A61K 35/745* (2015.01)
*A61K 35/744* (2015.01)
*A23L 33/135* (2016.01)
*A61P 21/00* (2006.01)
*A61K 35/00* (2006.01)

(52) U.S. Cl.
CPC .......... *A61K 35/745* (2013.01); *A23L 33/135* (2016.08); *A61K 35/744* (2013.01); *A61P 21/00* (2018.01); *A61K 2035/115* (2013.01)

(58) Field of Classification Search
CPC ................ A61K 35/745; A61K 35/744; A61K 2035/115; A23L 33/135; A61P 21/00
USPC ....................................... 424/93.44
See application file for complete search history.

(56) References Cited

FOREIGN PATENT DOCUMENTS

| AU | 2015100928 | 10/2015 |
|----|------------|---------|
| EA | 200101262 A1 | 4/2002 |
| WO | WO 2011/110918 | 9/2011 |

OTHER PUBLICATIONS

Mintel, "Superfruit Probiotic + Prebiotic Enhanced Berverage", XP055294747, retrieved from http://www.gnpd.com/sinatra/recordpage/3448303/from_search/dTVzilsVw9/?page=1 Database accession No. 3448303, Sep. 30, 2015.
Mintel, "Lactic Acid Bacteria Capsule with Vitamins B, C & D", XP055294748, retrieved from http://www.gnpd.com/sinatra/recordpage/2318724/from_search/0KxXrvRPnL/?page=1 Database accession No. 2318724, Feb. 28, 2014.
Shing et al., Effects of probiotics supplementation on gastrointestinal permeability, inflammation and exercise performance in the heat, European Journal of Applied Physiology, 2013: 114(1); 93-103.
Hawley et al., "Carbohydrate Dependence During Prolonged, Intense Endurance Exercise", Sports Med, 2015, 45 (Suppl 1):S5-S12.
Latvala et al., "Lactobacillus rhamnosus GG and *Streptococcus thermophilus* induce suppressor of cytokine signalling 3 (SOCS3) gene expression directly and indirectly via interleukin-10 in human primary macrophages", Clinical and Experimental Immunology, 2011, 165: 94-10.

*Primary Examiner* — Jennifer M. H. Tichy
(74) *Attorney, Agent, or Firm* — James S. Keddie; Bozicevic, Field & Francis LLP

(57) ABSTRACT

The present invention relates to a bacterial composition which can be effectively used in the field of sport nutrition, since it is capable of attenuating the decline in sport performance in a subject after a muscle-damaging exercise.

5 Claims, 3 Drawing Sheets

BACTERIAL COMPOSITION FOR USE IN ATTENUATING THE DECLINE IN PERFORMANCE AFTER EXERCISE

CROSS-REFERENCE TO RELATED APPLICATIONS

This application is a § 371 national phase of International Application No. PCT/IB2016/056919, filed on Nov. 17, 2016, which claims the benefit of Italian Patent Application No. 102015000074653, filed on Nov. 19, 2015, which applications are incorporated by reference herein.

The present invention relates to a bacterial composition, which is effectively used in the field of sport nutrition, since is capable of attenuating the decline in sport performance of a subject after exercise.

An intense and prolonged sport activity is known to lead to an effort, which can even cause a more or less marked damage to the fibers of muscles subjected to said effort, depending on the intensity thereof. Furthermore, an intense and prolonged sport practice results in an overall inflammatory response by the immune system, which reacts to the muscle damages being caused. Under this circumstance, sport performances are reduced with an inevitable drop of efficiency.

A strenuous and infrequent exercise, especially with a marked eccentric component, can lead to exercise-induced muscle damage (EIMD). Research demonstrated that the eccentric exercise induces EIMD in that the muscle is subjected to excessive forced stretching and contraction, which exacerbate the mechanical overload, thereby causing a muscle injury as a microtrauma. EIMD symptoms comprise: delayed onset muscle soreness (DOMS), reduced resistance, swelling, increased concentrations of creatine kinase due to the cell membrane destruction, weakened vascular function, and reduced glucose supply. These symptoms occur at any moment from 24 hours up to 7 days after exercise and are related to an increase of both inflammation and circulating leukocytes. The injured muscle attracts leukocytes in the area, and neutrophils and macrophages thus release ROS and pro-inflammatory cytokines in order to repair the damaged area. TNF-α is responsible for muscle proteolysis, and is upregulated by IL-6. Other cytokines such as NF-κβ are also stimulated by ROS. The damaged tissue is thus repaired and adapted, becoming more resistant to subsequent eccentric loads being applied.

By "muscle damage" is thus meant the loss of functionality of one or more muscles, which can be temporary, i.e. destined to be completely recovered within a more or less long period of time via the normal physiological processes for repairing muscle tissues, or it may have permanent effects of reduced, even partial, functionality.

By "exercise" is meant a sport, recreational, playing, working, locomotor or different activity, which comprises muscular movements and is, at least potentially, able to provoke a muscle injury, as defined above, in subjects performing it, in particular, but not limited to subjects with no specific training for such muscular movements.

Therefore, it would be very useful to have a natural, effective, easy-to-take remedy devoid of side effects for health, intended for all the subjects performing a strenuous and infrequent sport or exercise.

The Applicant, following to an intense and prolonged research and development activity, suitably met the above-cited needs.

It is an object of the present invention a composition for use in sport practice having the characteristics as set forth in the appended claims.

It is an object of the present invention the non-therapeutic use of a composition comprising a mixture which comprises or, alternatively, consists of at least a strain of bacteria belonging to the species *Bifidobacterium breve* and at least a strain of bacteria belonging to the species *Streptococcus thermophilus* for attenuating or reducing or eliminating the decline in performance after exercise, wherein said use comprises the oral administration of said composition to a subject who performed said exercise.

*Bifidobacterium breve* BR03 culture was deposited on Jul. 20, 2004, to the Deutsche Sammlung Von Mikroorganismen Und Zellkulturen GmbH (DSMZ) with the accession No. DSM 16604.

*Streptococcus thermophilus* FP4 culture was deposited on Sep. 13, 2006, to the DSMZ with the accession No. DSM 16604.

The DSMZ is located at Inhoffenstr. 7B, D-3 8124 Braunschweig.

It is an object of the present invention a composition comprising a mixture which comprises or, alternatively, consists of at least a strain of bacteria belonging to the species *Bifidobacterium breve* and at least a strain of bacteria belonging to the species *Streptococcus thermophilus* said composition being for use in the curative and/or preventive treatment of muscular pain, muscle soreness, muscle inflammation, muscle fatigue and/or muscle degeneration, in increasing the amount of muscle energy and improving the mitochondrial functions in a deficient subject.

It is an object of the present invention a composition comprising a mixture, which comprises or, alternatively, consists of the strains of bacteria *Bifidobacterium breve* BR03 (DSM 16604) and *Streptococcus thermophilus* FP4 (DSM 18616), preferably in a weight ratio of 1:1 and preferably in an amount of $5 \times 10^9$ CFU/g, each strain.

Figure 1:
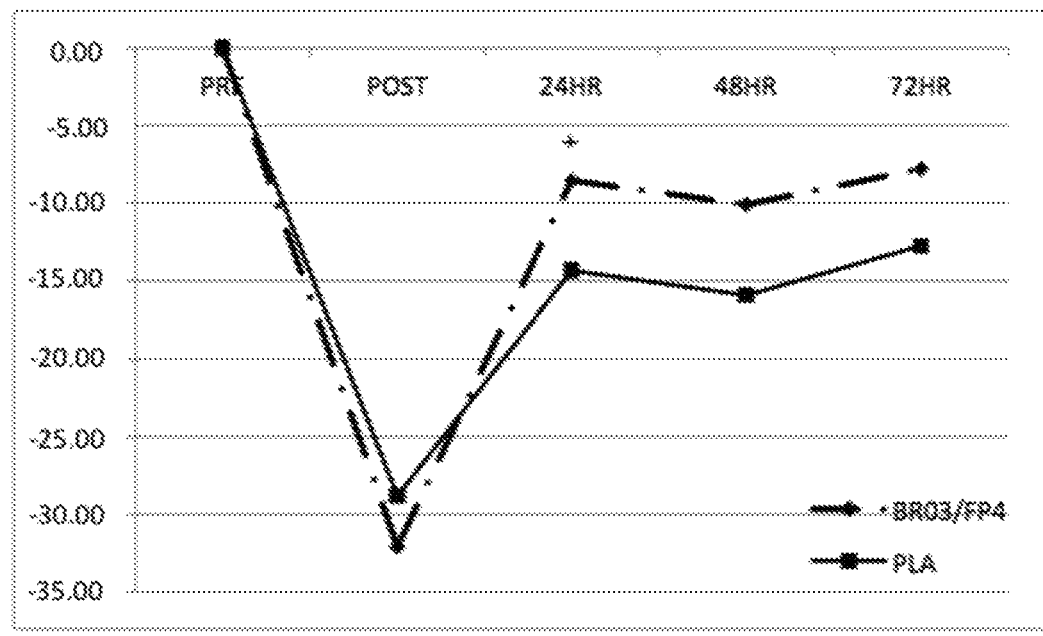
FIG. 1 is a graph showing the percentage change in peak torque during the isometric flexion of the elbow.
Figure 2:
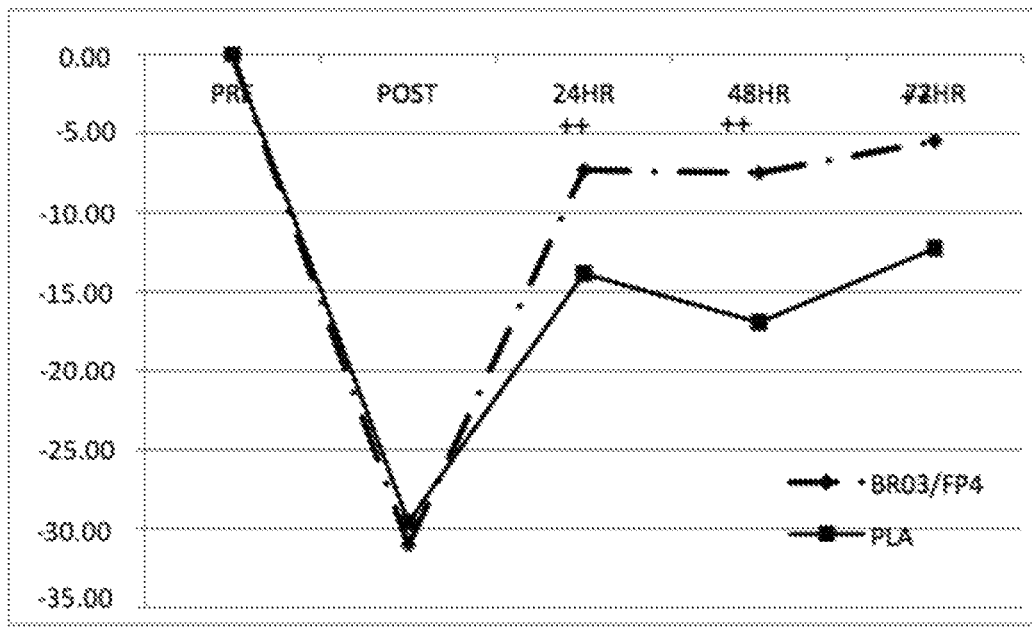
FIG. 2 is a graph showing the percentage change in average peak torque during the isometric flexion of the elbow.
Figure 3:
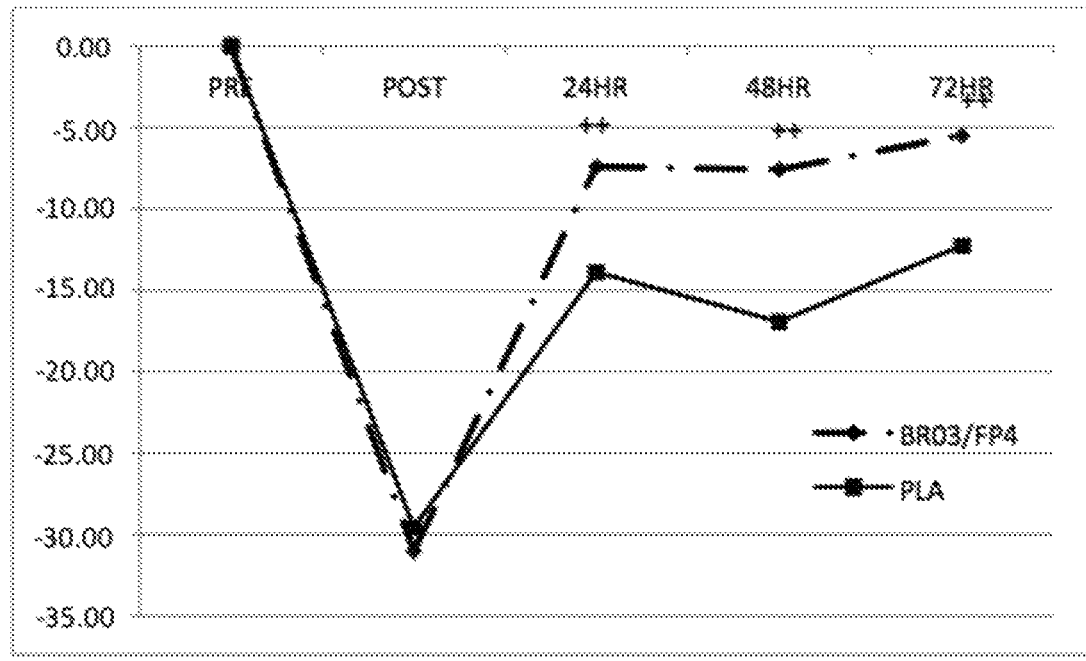
FIG. 3 is a graph showing the average peak torque relative to the body weight, during the isometric flexion of the elbow.
Figure 4:
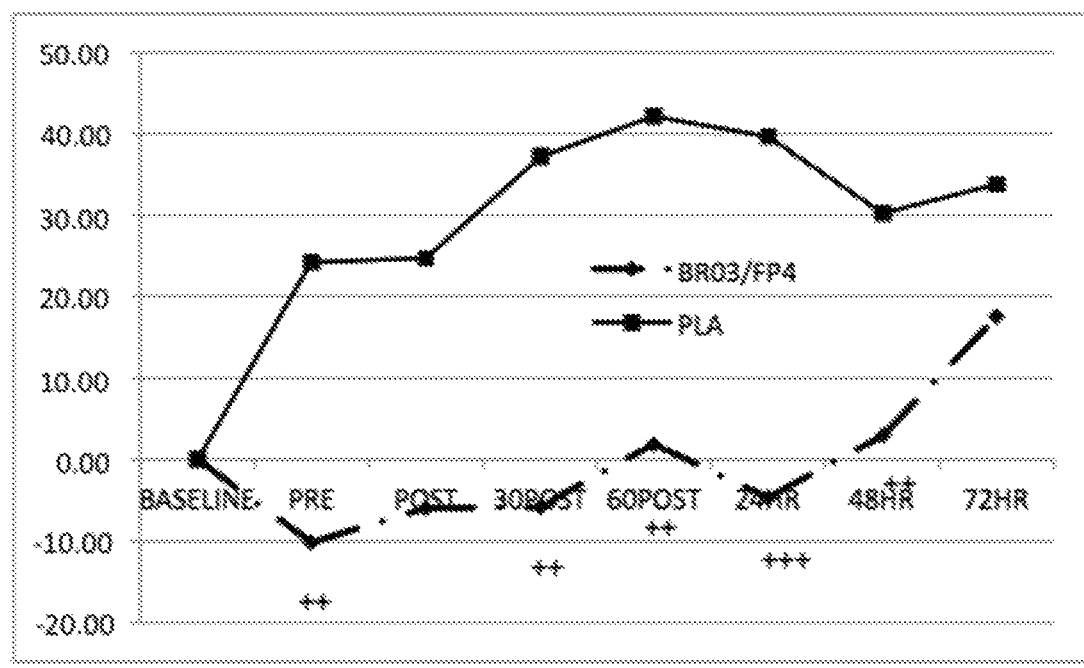
FIG. 4 is a graph showing the likelihood there being a different in results. Likelihood is shown as an increased occurrence of symbols(+) relative to placebo (PLA): +possible, ++likely, +++very likely, ++++highest likelihood.

Preferred embodiments of the present invention are hereinafter illustrated in detail by way of example and, therefore, without limiting the scope thereof.

Within the context of the present invention by the composition(s) of the present invention is meant to encompass pharmaceutical compositions, compositions for medical devices, compositions for supplement products as well as food, nutraceutical and functional compositions.

The Applicant developed a composition comprising a mixture which comprises or, alternatively, consists of at least a strain of bacteria belonging to the species *Bifidobacterium breve* and at least a strain of bacteria belonging to the species *Streptococcus thermophilus*, said composition being for use in attenuating or reducing or eliminating the decline in sport performance after exercise, which can lead to a muscle damage.

The strains of bacteria belonging to the species *Bifidobacterium breve*, being object of the present invention, are selected due to their capability to inducing the synthesis of Interleukin 10 (IL-10), which exerts an anti-inflammatory effect pro-Th2, in order to act and re-establish a proper Th1/Th2 ratio (balance).

The strains of bacteria belonging to the species *Streptococcus thermophilus*, being object of the present invention, are selected due to their capability, along with the strains of bacteria belonging to the species *Bifidobacterium breve*, to inducing the reduction/decrease of Interleukin 6 (IL-6), which exerts a pro-inflammatory effect pro-Th1, in order to act and re-establish a proper Th1/Th2 ratio (balance).

The Applicant carried out an accurate selection of some species of bacteria belonging to the genus *Lactobacilli* and *Bifidobacteria* and, after several attempts, succeeded to detect the species *Bifidobacterium breve* and the species *Streptococcus thermophilus*.

Advantageously, among the many strains of bacteria belonging to the species *Bifidobacterium breve*, the strain of bacteria *Bifidobacterium breve* BR03 (DSM 16604) deposited on 20 Jul. 2004 by Anidral Srl (presently Probiotical SpA) showed to be very interesting in inducing the increase of IL-10, an anti-inflammatory cytokine. The selected strains of bacteria *B. breve*, being object of the present invention, among which the strain of bacteria *Bifidobacterium breve* BR03, induce a marked increase of T helper lymphocytes and the secretion of Th2 cytokines (IL-10 and IL-4) and also have a remarkable anti-inflammatory property due to the shift of the Th1/Th2 balance towards a Th2 response.

Advantageously, among the many strains of bacteria belonging to the species *Streptococcus thermophilus*, the strain of bacteria *Streptococcus thermophilus* FP4 (DSM 18616) deposited on 13 Sep. 2006 by Mofin Srl showed to be very interesting in inducing the reduction of IL-6, a pro-inflammatory cytokine. The selected strains of bacteria *S. thermophilus*, being object of the present invention, among which the strain of bacteria *Streptococcus thermophilus* FP4 (DSM 18616), induce a marked reduction of cytokines Th1 (IL-6) secretion, which shifts the Th1/Th2 balance towards a Th1 response.

Advantageously, the supplementation with a composition of the present invention which comprises a mixture comprising or, alternatively, consisting of a strain of bacteria *Bifidobacterium breve* BR03 (DSM 16604) and a strain of bacteria *Streptococcus thermophilus* FP4 (DSM 18616) is capable of reducing inflammation, by lowering the inflammatory response and attenuating the decline in performance after exercise. The two strains of bacteria are present in the mixture in a weight ratio of 1:1, or 2:1, or 3:1, or 4:1, or 1:2, or 1:3, or 1:4.

The composition of the present invention can further comprise additives, flavors, pH stabilizers and excipients or ingredients of pharmaceutical or food grade.

The strains of bacteria can be coated, encapsulated, or filmed, with a lipid layer, for example a plant lipid layer, in order to favoring both the intake and the absorption, for example at intestinal level. The strains of bacteria belonging to the species *Bifidobacterium breve* and the species *Streptococcus thermophilus* are present in a concentration comprised from $1 \times 10^6$ to $1 \times 10^{11}$, preferably from $1 \times 10^7$ to $1 \times 10^{10}$, even more preferably from $1 \times 10^8$ to $1 \times 10^9$ CFU/g, based on the total weight of the composition according to the present invention.

It is an object of the present invention a composition comprising a mixture, which comprises or, alternatively, consists of the strains of bacteria *Bifidobacterium breve* BR03 (DSM 16604) and *Streptococcus thermophilus* FP4 (DSM 18616) in a weight ratio of 1:1.

Advantageously, the composition of the present invention is effectively used in the event of prolonged exercise, which damages the muscle fibers.

Advantageously, said composition can be for therapeutic use, namely in subjects which experienced a muscle injury or are at risk thereof or, alternatively, for non-therapeutic use, i.e. for subjects who do not suffer from a specific pathological condition and are not at specific risk to contracting it.

It is an object of the present invention the non-therapeutic use of a composition comprising a mixture which comprises or, alternatively, consists of at least a strain of bacteria belonging to the species *Bifidobacterium breve* and at least a strain of bacteria belonging to the species *Streptococcus thermophilus* for attenuating or reducing or eliminating the decline in performance after exercise, which can even cause a muscle injury, wherein said use comprises the oral administration of said composition to a subject who performed an exercise, that can be also able to provoke muscle damages.

Advantageously, said use is for non-therapeutic purposes, i.e. is not related to the therapeutic or preventive treatment of diseases or disorders, in particular involving the musculature, in subjects suffering from such diseases or disorders and/or at risk to contracting them.

In a preferred embodiment, in the use according to the present invention, the composition comprises a strain of bacteria belonging to the species *Bifidobacterium breve*, which is the strain of bacteria *Bifidobacterium breve* BR03 deposited at the DSMZ Institute with the No. DSM 16604 and/or a strain of bacteria belonging to the species *Streptococcus thermophilus*, which is the strain of bacteria *Streptococcus thermophilus* FP4 deposited at the DSMZ Institute with the No. DSM 18616.

In a preferred embodiment, in the use according to the present invention, the composition comprises strains of bacteria belonging to the species *Bifidobacterium breve*, such as the strain of bacteria *Bifidobacterium breve* BR03 deposited at the DSMZ Institute with the No. DSM 16604, and strains of bacteria belonging to the species *Streptococcus thermophilus*, such as the strain of bacteria *Streptococcus thermophilus* FP4 deposited at the DSMZ Institute with the No. DSM 18616, which are present in a concentration comprised from $1 \times 10^6$ to $1 \times 10^{11}$, preferably from $1 \times 10^7$ to $1 \times 10^{10}$, even more preferably from $1 \times 10^8$ to $1 \times 10^9$ CFU/g.

In a preferred embodiment, in the use according to the present invention, the composition comprises strains of bacteria belonging to the species *Bifidobacterium breve*, such as the strain of bacteria *Bifidobacterium breve* BR03 deposited at the DSMZ Institute with the No. DSM 16604, and strains of bacteria belonging to the species *Streptococcus thermophilus*, such as the strain of bacteria *Streptococcus thermophilus* FP4 deposited at the DSMZ Institute with the No. DSM 18616, which are present in a weight ratio of 1:1, or 2:1, or 3:1, or 4:1, or 1:2, or 1:3, or 1:4; preferably 1:1.

In a preferred embodiment, said strains of bacteria are in encapsulated form, i.e. coated with at least a lipid layer. As a non-limiting example, said lipid layer can be of plant origin and/or having a melting point comprised from 40 to 60° C.

In a preferred embodiment, in the use according to the present invention, the composition comprises the strains of bacteria *Bifidobacterium breve* BR03 (DSM 16604) and *Streptococcus thermophilus* FP4 (DSM 18616), more preferably wherein said strains are in a weight ratio of 1:1, more preferably coated with a lipid layer as described above.

In a preferred embodiment, in the use according to the present invention, the composition advantageously enhances exercise during training and sport practice.

In a preferred embodiment, in the use according to the present invention, the exercise is an intense and prolonged sport activity, which results in an effort damaging the muscle fibers and/or musculature in general.

Alternatively, the composition can be for therapeutic use, namely for alleviating or preventing muscle damages in subjects who performed efforts, which can potentially damage the muscle tissues.

It is an object of the present invention a composition comprising a mixture which comprises or, alternatively, consists of at least a strain of bacteria belonging to the species *Bifidobacterium breve* and at least a strain of bacteria belonging to the species *Streptococcus thermophilus*; said composition being for use in the curative and/or preventive treatment of muscular pain, muscle soreness, muscle inflammation, muscle fatigue and/or muscle degeneration, in increasing the amount of muscle energy or improving the mitochondrial functions in a deficient subject.

In a preferred embodiment, in the composition for use according to the present invention, said strain of bacteria belonging to the species *Bifidobacterium breve* is the strain of bacteria *Bifidobacterium breve* BR03 deposited at the DSMZ Institute with the No. DSM 16604, and/or wherein said strain of bacteria belonging to the species *Streptococcus thermophilus* is the strain of bacteria *Streptococcus thermophilus* FP4 deposited at the DSMZ Institute with the No. DSM 18616.

In a preferred embodiment, in the composition for use according to the present invention, said strains of bacteria belonging to the species *Bifidobacterium breve* and the species *Streptococcus thermophilus* are present in a concentration comprised from $1\times10^6$ to $1\times10^{11}$, preferably from $1\times10^7$ to $1\times10^{10}$, even more preferably from $1\times10^8$ to $1\times10^9$ CFU/g.

In a preferred embodiment, in the composition for use according to the present invention, said strains of bacteria *Bifidobacterium breve* and *Streptococcus thermophilus* are present in a weight ratio of 1:1, or 2:1, or 3:1, or 4:1, or 1:2, or 1:3, or 1:4.

In a preferred embodiment, said strains of bacteria are in encapsulated form, namely coated with at least a lipid layer. As a non-limiting example, said lipid layer can be of plant origin and/or having a melting point comprised from 40 to 60° C.

In a preferred embodiment, in the composition for use according to the present invention, said strains of bacteria *Bifidobacterium breve* BR03 (DSM 16604) and *Streptococcus thermophilus* FP4 (DSM 18616) are preferably in a weight ratio of 1:1, more preferably coated with a lipid layer as described above.

In a preferred embodiment, said composition for use according to the present invention enhances the overall immune response by the immune system.

In a preferred embodiment, said composition for use according to the present invention reduces the overall inflammatory response by the immune system.

In a preferred embodiment, said composition for use according to the present invention is able to shift the Th1/Th2 balance towards a Th2 response.

It is an object of the present invention the following preferred embodiments (PE 1-10):

PE 1. A composition comprising a mixture which comprises or, alternatively, consists of at least a strain of bacteria belonging to the species *Bifidobacterium breve* and at least a strain of bacteria belonging to the species *Streptococcus thermophilus*; said composition being for use in attenuating or reducing or eliminating the decline in performance after muscle-damaging exercise.

PE 2. The composition for use according to PE 1, wherein said strain of bacteria belonging to the species *Bifidobacterium breve* is the strain of bacteria *Bifidobacterium breve* BR03 deposited at the DSMZ Institute with the No. DSM 16604.

PE 3. The composition for use according to PE 1 or 2, wherein said strain of bacteria belonging to the species *Streptococcus thermophiles* is the strain of bacteria *Streptococcus thermophilus* FP4 deposited at the DSMZ Institute with the No. DSM 18616.

PE 4. The composition for use according to any one of PE 1-3, wherein the exercise is an intense and prolonged sport activity, which results in an effort damaging the muscle fibers and/or musculature in general.

PE 5. The composition for use according to any one of PE 1-4, wherein the strains of bacteria belonging to the species *Bifidobacterium breve* and the species *Streptococcus thermophilus* are present in a concentration comprised from $1\times10^6$ to $1\times10^{11}$, preferably from $1\times10^7$ to $1\times10^{10}$, even more preferably from $1\times10^8$ to $1\times10^9$ CFU/g.

PE 6. The composition for use according to any one of PE 1-5, wherein the strains of bacteria *Bifidobacterium breve* BR03 (DSM 16604) and *Streptococcus thermophilus* FP4 (DSM 18616) are present in a weight ratio of 1:1, or 2:1, or 3:1, or 4:1, or 1:2, or 1:3, or 1:4.

PE 7. The composition for use according to any one of PE 1-6, wherein said composition enhances the overall immune response by the immune system.

PE 8. The composition for use according to any one of PE 1-6, wherein said composition reduces the overall inflammatory response by the immune system.

PE 9. The composition for use according to any one of PE 1-6, wherein said composition improves exercise during training and sport practice.

PE 10. The composition for use according to any one of PE 1-6, wherein said composition is able to shift the Th1/Th2 balance towards a Th2 response.

The following examples are provided in order to illustrate practical embodiments of the invention, without whishing to limit the aim thereof.

EXPERIMENTAL PART

1. Summary

In order to determine the effect of a composition of the present invention comprising a mixture based on a strain of bacteria *Bifidobacterium breve* BR03 (DSM 16604) and a strain of bacteria *Streptococcus thermophilus* FP4 (DSM 18616) on the inflammatory response and the subsequent performance following to an intense period of muscle-damaging exercise, repeated, randomized, double-blind, placebo-controlled two-way measurements were used. The composition according to the invention reduces the inflammation and allows a greater adaptation to the training and subsequent increases in sport performances. The effect of the intake of said composition on inflammation and muscle performance following to an intense period of muscle-damaging exercise was studied.

The randomized, double-blind, placebo-controlled cross-over method was applied to sixteen healthy resistance-trained men (25±4 years; 177.9±8.5 cm; 81.1±10.3 kg) which daily took the composition with the strains of bacteria in encapsulated form, said composition containing $5\times10^9$ CFU/g of B. breve BR03 (DSMZ 16604) and $5\times10^9$ CFU/g of S. thermophilus FP4 (DSMZ 18616) (PRO) or placebo (PLA) before performing (21 days) an exercise, which damages the elbow flexors.

The performance of elbow flexors and an inflammatory marker (interleukin-6) were measured before and after the muscle-damaging exercise. A 21-day wash-out period separated the conditions. A standardized magnitude-based inference to define outcomes was used.

The effects of both the treatment and time on the dependent variables of interest by a mixed model ANOVA using SPSS V.22 (IBM Corporation; Armonk, N.Y.) were assessed. The approach to the magnitude-based inference was used. This approach allows to solving problems concerning the estimates of the extent of the effect of a large sample with reference to precision (width of the confidence interval) relative to the minimal significant change for the considered outcome.

Results advantageously show that the intake of the composition, being object of the present invention, with the strains of bacteria in encapsulated form (strains coated with a single lipid coating of plant origin having a melting point comprised from 40° C. to 60° C.) containing $5\times10^9$ CFU/g of B. breve BR03 (DSMZ 16604) and $5\times10^9$ CFU/g of S. thermophilus FP4 (DSMZ 18616) attenuated the decline in performance at 24 (effect size [ES]=0.3), 48 (ES=0.5) and 72 hours (ES=0.3) post-exercise, measured by the average peak torque. Said composition exhibited an overall anti-inflammatory effect (ES=0.5).

Advantageously, the supplementation with said tested composition attenuates the decline in performance and subsequent inflammation following to an intense period of muscle-damaging exercise. The composition of the present invention is capable of attenuating or reducing or eliminating the decline in performance after exercise, typically observed after an intense period of muscle-damaging exercise and decreasing the related inflammatory response, measured by interleukin-6 (IL-6).

2. Subjects

The inclusion criteria in the study comprised: (1) attending to structured resistance training for 1 year before the test; (2) abstaining from nutritional supplement products or ergogenic aids during the 6 weeks before the test; and (3) abstaining from anti-inflammatory drugs during the previous month.

The study was carried out according to the guidelines of the Helsinki Declaration and registered at ClinicalTrials.gov: NCT02520583).

All the procedures involving human subjects were approved by the Institutional Review Board at Texas Christian University for the use of human subjects in research (protocol No. 1501-009-1502). All the subjects provided a written consent.

3. Experimental protocol

A randomized, double-blind, placebo-controlled crossover research design for determining the effect of a first administration of probiotic strains B. breve BR03 and S. thermophilus FP4 on the subsequent performance and the acute inflammatory response following to a training session with muscle damage was used. Prior to the experimental test, a basal blood sample was taken from fasting subjects, before to be randomly assigned to orally intake for 21 days, as a supplement product, either a probiotic composition containing a mixture of 5 billions of live cells (AFU) of S. thermophilus FP4 (DSMZ 18616) and 5 billions of live cells (AFU) of B. breve BR03 (DSMZ 16604) (Probiotical S.p.A., Novara, Italy; Probiotic), based on a previous dose regimen study, or a placebo.

Materials of the study were analyzed by Biolab Research S.r.l., Novara, Italy, through flow cytometry (Biolab research method 612-04, standardized by ISO 19344: 2015 IDF 232: 2015 and accredited by Accredia, Roma, Italy, >10 billions of live cells), and the plate count method (Biolab Research method 031-08, >10 billions CFU), confirming the count of the target cells.

At least 72 hours before the experimental test, subjects were familiarized with the procedure of experimental assessment (isometric strength).

The first experimental test started at least 21 days after the beginning of the probiotic or placebo administration. Subjects were instructed to abstain from any non-daily living activity during the 72 h before the test.

Furthermore, subjects were instructed to abstain from any food, which could interfere with the study procedures. The day of the experimental test, the subjects, fasting from at least 8 h, were placed in a supine position for inserting the catheter in order to allowing multiple blood withdrawals. After taking a basal blood sample, the upper arm circumference, range of motion and pain of the subjects were assessed prior to a warm-up, followed by the determination of the isometric strength.

Then the subjects performed a session of eccentric exercises of the elbow flexors, which are known to cause muscle damages. The initial limb was randomly selected. Immediately after the eccentric exercise, a second blood sample was taken, and the isometric strength was determined again. Subjects were thus placed in a supine position for 60 min. Blood samples were obtained 30 min and 60 min after the session of eccentric exercise. One hour post-exercise, the upper arm circumference, range of motion, and pain were assessed again.

Subjects were re-examined at 24, 48, and 72 hours following to the session of eccentric exercise for a blood withdrawal, and the assessment of the upper arm circumference, range of motion, and pain, followed by the determination of the isometric strength. After a 21-day wash-out, subjects repeated the experimental protocol with administration of the supplement product alternative to that previously taken (namely, who previously received the placebo, took the probiotic in the second session, and vice versa) and using the contralateral limb.

3.1 Isometric peak

The maximal voluntary isometric peak torque of the elbow flexors was measured at a joint angle of 90° on an isokinetic dynamometer (Biodex System 3, Shirley, N.Y., USA). Prior to determining the maximal isometric torque, subjects performed a warm-up of 2 sets of 3 repetitions, from 60° to 180° at two different speeds (90° $s^{-1}$ and 60° $s^{-1}$, respectively) resting for 30 s between sets. Then, subjects performed two tests of maximal isometric torque of elbow flexors, each of 4 s separated by 30 s of rest between tests. Verbal encouragement as well as a real-time display of power were provided throughout the exercise for encouraging the achievement of the maximum efforts.

3.2 Eccentric exercise protocol

Following to a warm-up and the determination of the isometric strength, subjects performed 5 sets of 10 maximal eccentric contractions (forced stretching) at a speed of 30°×s⁻1. After every forced eccentric contraction, from 60° to 180°, the research staff brought the arm back to the starting position at a speed of $10° s^{-1}$ (12 s), so that no concentric contraction was performed by the subject. Sets were one minute-separated, and subjects were encouraged throughout the exercise. The same research technician was assigned for all the studies involving the same subject.

3.3 Blood test

At the day of the eccentric exercise session, subjects were placed in a supine position for inserting the catheter. The area was sterilized according to standard withdrawal procedures and a catheter (BD Biosciences, San Jose, Calif., USA) was inserted in an antecubital vein and capped for multiple blood withdrawals. The catheter was kept patent by fluxing 2-3 ml of 0.9% sodium chloride (G-Biosciences, St. Louis, Mo., USA) injected in the withdrawal site.

Prior to each blood withdrawal from the catheter, a 3 mL Vacutainer (BD Biosciences, San Jose, Calif., USA) was used for taking a sample to be discarded. A blood sample is obtained before starting the administration of the test composition and 21 days later, prior to the performance of the eccentric exercise session. Since then, blood was immediately taken post-exercise and 30 min and 60 min later. Blood samples were also withdrawn at 24, 48 and 72 h post-exercise. Blood samples were collected in 10 mL EDTA tubes (BD Biosciences, San Jose, Calif., USA).

Blood samples were centrifuged by 30 min from collection for 20 min at 2000× g in a refrigerated centrifuge (4° C.). Plasma aliquots were then immediately transferred and frozen at −80° C. until further analyses. The plasma samples were analyzed for IL-6 concentrations by using a human IL-6 high sensitivity ELISA Kit (R & D Systems, Minneapolis, Minn., USA). The detection range for this test was from 0.156 pg. mL¹ to 10 pg. pg. mL¹. The inter- and intra-assay coefficients of variation for each test were of less than 10%.

3.4 Data presentation and transformation

Raw data are presented as mean and standard deviation. All the data, except for visual analog scale data, were log-transformed before analysis for managing a non-uniformity of error. The treatment effects and the treatment x time on outcomes were assessed by a mixed-model analysis of variance (Proc Mixed, SAS 9.4, Cary, N.C., USA), with the subject term as the random effect. Estimates of log-transformed analysis were presented as back log-transformed least-squares means or adjusted geometric means with uncertainty (90% confidence interval, CI).

3.5 Statistical inference

As regards inference, a magnitude-based approach was used. A numerical translation of performances in the experimental model to the actual power of performance is unknown, with the isometric torque as the research design for investigating the proof of principle. Therefore, the smallest standardized difference was considered the smallest main change for the primary and related mechanistic results. In the present case, the magnitude threshold for the smallest change was the Glass'd standardized difference (0.2×the baseline SD for the control condition).

The likelihood that a contrast was at least greater than the relative thresholds was of 25%-75% for low likelihood, 75%-95% likely, 95%-99.5% very likely, >99.5% almost certain. If most (>50%) of the confidence interval (IC) occurred between thresholds for a positive and negative substantiality, the effect was scored as trivial (negligible). The terms beneficial, trivial, and harm relate to the most likely directional result, relative to the minimal effect threshold. The term unclear relates to outcomes wherein the likelihood is greater than 5% for both benefits and damages.

3.6 Isometric peak torque

Figure 5A:
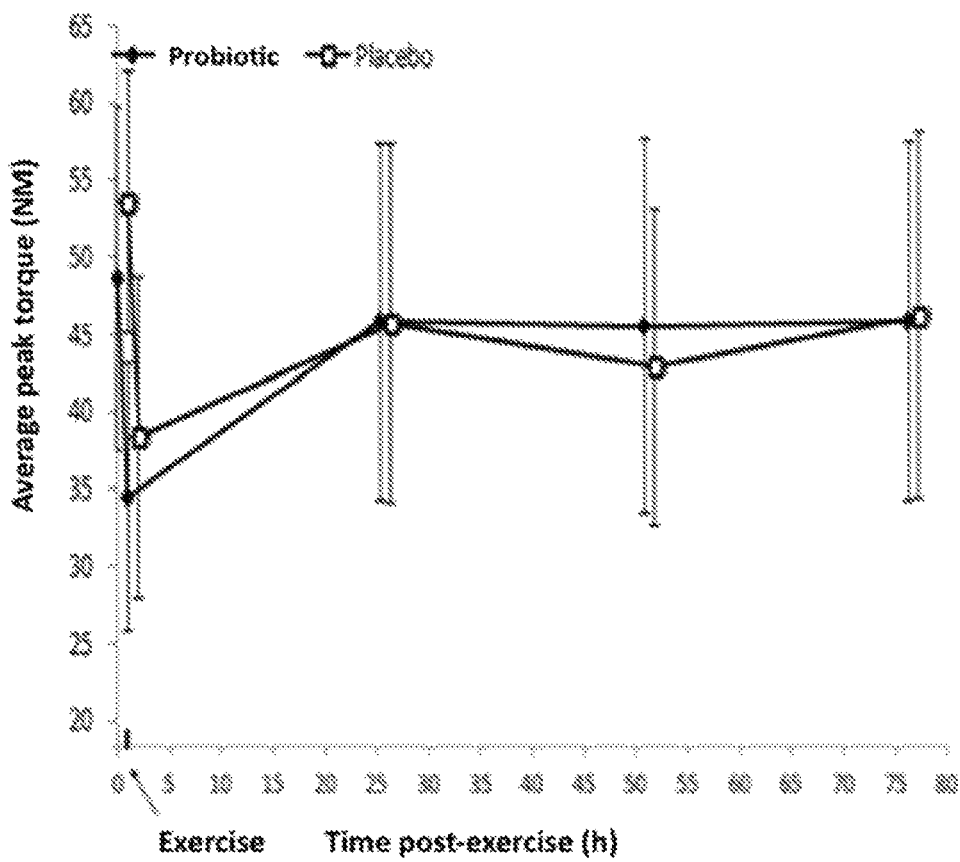
FIG. 5a is a graph showing the effect of a 21-day administration of probiotics and placebo on the mean isometric peak torque before and during 72 hours following to the eccentric load of the exercise.

After the 21-day supplementation, the average peak torque was significantly lower (13.8%; 90% CI 25.4, 3.3%) following to probiotics relative to placebo (FIG. 5A). Decline in performance was observed after exercise under both the conditions, proving the efficacy of the damage-inducing protocol.

Figure 5B:
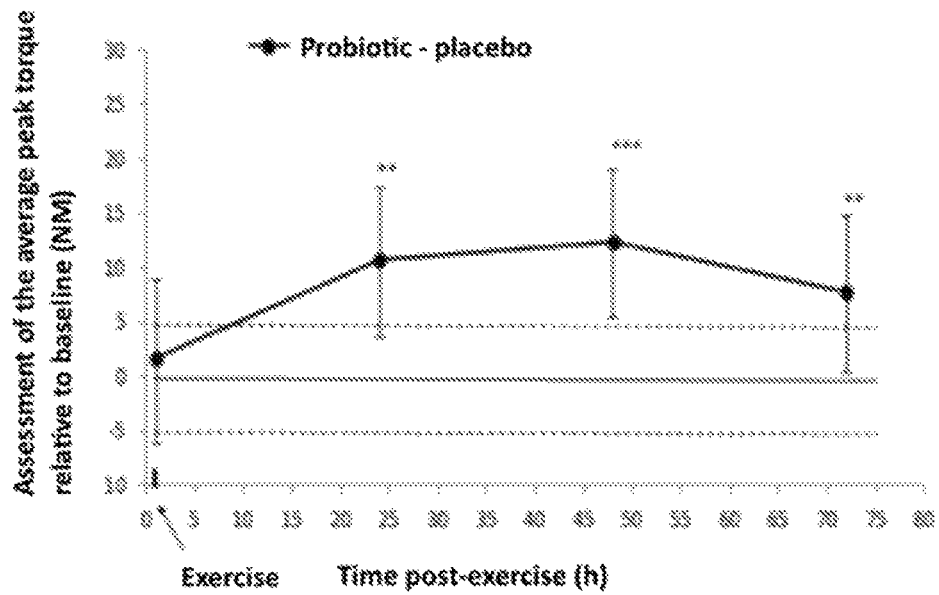
FIG. 5b is a graph showing the probiotic-placebo difference with an adjusted score for the basal value (pre-eccentric exercise).

The administration of the composition according to the invention significantly enhanced the production of maximal mean isometric torque at 24 and 72 hours after the harmful physical activity, as compared to pre-exercise (FIG. 5B. probiotic-placebo effect and 90% CI, likelihood % benefit/trivial/harms:

24 h, 11% 90% CI 17.4%, 92.5/7.4/048;
48 h, 12% 90% CI 19.55%, 96.5/3.5/0;
72 h, 8% 90% CI 15.0%, 77.3/22.4/0.3).

FIG. 5*a* shows the effect of a 21-day administration of probiotics and placebo on the mean isometric peak torque before and during 72 hours following to the eccentric load of the exercise. FIG. 5*b* shows the probiotic-placebo difference with an adjusted score for the basal value (pre-eccentric exercise). Data in FIG. 5*a* are the raw means and SD. Data in FIG. 5*b* are the probiotic-placebo effect as placebo percentage and 90% confidence intervals derived from the mixed-model analysis of variance.

Horizontal dotted lines are the smallest thresholds of standardized difference (+4.5%), whereas the likelihood of substantial change is included above the contrast represented by =likely; *=very likely; outcomes with no stars are inconclusive or unclear.

4. Discussion

The main finding of the present study was that the 21-day administration of probiotics according to the invention attenuated the decline in performance following to an exercise session which causes, or can cause, muscle damaging.

The administration of probiotics according to the present invention leads to a greater resting arm angle relative to placebo. It was proved that the administration of prebiotics according to the invention actually increases the resting arm angle as compared to placebo at 24 and 48 hours.

IL-6 concentration decreases following to the 21-day administration of probiotics according to the invention, while no increase with placebo was observed.

Data of the present study show that the prebiotic administration, without a concurrent administration of proteins, attenuates the decline in muscle performance, since a greater isometric peak torque was observed relative to placebo during the several recovery days after eccentric contractions of stretching. It follows that with the composition according to the invention the administration of prebiotics alone was shown for the first time to attenuate the decline in muscle performance.

Specific reference to FIGS. 1, 2, 3 and 4 is made.

The percentage change in peak torque (FIG. 1), average peak torque (FIG. 2), and average peak torque relative to the body weight (FIG. 3) during the isometric flexion of the elbow are shown below. The threshold for the minimal substantial change was calculated as 0.2 times the baseline $SD_{between}$. Likelihood is shown as an increased occurrence of symbols (+) relative to placebo (PLA):+possible, ++likely, +++very likely, ++++highest likelihood. All the data are an average.

The reduction of about 30% in the ability of power generation underlines the efficacy of the muscle-damaging protocol in stimulating the required response. The supplementation with the tested composition (p=0.199) attenuated the decline in performance observed after a muscle-damaging exercise, 24 hours after an intense exercise period (FIG. 1). With the average peak torque, a benefit at 24 hours (p=0.111), 48 hours (p=0.046), and 72 hours (p=0.194) was observed. Similarly, the average peak torque relative to the body weight showed a benefit from the supplementation of the tested composition at 24 hours (p=0.117), 48 hours (p=0.050), and 72 hours (p=0.198).

Inflammation was assessed by changes in IL-6 following to an intense period of muscle-damaging exercise. However, since the effect of the tested composition in decreasing the overall inflammatory response, IL-6 was evaluated at the baseline before the supplementation period. Indeed, supplementation with the strains of bacteria *B. breve* BR03 (DSMZ 16604) and *S. thermophilus* FP4 (DSMZ 18616) provided a reduction effect on IL-6, as shown by a decrease in the percentage change from the baseline in subjects supplemented with said strains of probiotic bacteria (−10%) as compared to an increase after placebo (24%). Furthermore, the difference (contrast) between the percentage change in IL-6 between placebo and probiotic was likely at 30 minutes (p=0.054), 60 minutes (p=0.056), and 48 hours (p=0.124) after muscle-damaging exercise, whereas it was probably lower (p=0.015) 24 hours later.

5. Conclusions

The 21-day administration of probiotics according to the invention, in healthy and resistance-trained subjects attenuates the decline in performance and range of motion following to a muscle-damaging exercise session. These data suggest that the oral administration of probiotics according to the invention can help in recovering the performances after an intense physical effort, even in untrained or poorly trained subjects.

From the above, it results that the composition of the present invention comprising a mixture which comprises or, alternatively, consists of at least a strain of bacteria belonging to the species *Bifidobacterium breve* and at least a strain of bacteria belonging to the species *Streptococcus thermophilus*, attenuates the decline in performance observed after a muscle-damaging exercise. This effect is due to a reduction of the overall inflammation, as confirmed by a decreased IL-6 after supplementation.

From a performance point of view, athletes attending to high-level training periods are known to lessen the ability of their immune system to counteract an infection. The supplementation with the composition of the present invention can, advantageously, lead to: 1) improving the overall immune response, thus 2) enhancing the performance during training thereby obtaining 3) a better performance during a competition. Furthermore, the obtained results involve additional healthy and positive effects since the supplementation with the selected strains of bacteria, being object of the present invention, is able to reduce the overall inflammatory response as shown in this pilot study. High IL-6 is found under chronic inflammatory conditions, which are known for also occurring in obesity-related diseases.

The invention claimed is:

1. A method for attenuating or reducing or eliminating a decline in performance after muscle damaging exercise, comprising orally administering a composition comprising a bacterial mixture consisting of bacteria belonging to the species *Bifidobacterium breve* and bacteria belonging to the species *Streptococcus* thermophiles, wherein the bacteria belonging to the species *Bifidobacterium breve* is *Bifidobacterium breve* BR03 deposited at the DSMZ Institute with the No. DSM 16604 and wherein the bacteria belonging to the species *Streptococcus thermophilus* is *Streptococcus thermophilus* FP4 deposited at the DSMZ Institute with the No. DSM 18616, to a subject who performed said muscle damaging exercise, and wherein the *Bifidobacterium breve* BR03 (DSM 16604) and *Streptococcus thermophilus* FP4 (DSM 18616) are present in the composition in a weight ratio of 1:1 and/or in an amount of $5\times10^9$ CFU/g, each strain.

2. The method of claim 1, wherein the bacteria in the composition are present in a concentration from $1\times10^6$ to $1\times10^{11}$, or from $1\times10^7$ to $1\times10^{10}$, or from $1\times10^8$ to $1\times10^9$ CFU/g.

3. The method of claim 1, wherein in the composition bacteria belonging to the species *Bifidobacterium breve* and the bacteria belonging to the species *Streptococcus thermophilus* are present in a weight ratio of 1:1, or 2:1, or 3:1, or 4:1, or 1:2, or 1:3, or 1:4.

4. The method of claim 1, wherein said muscle damaging exercise comprises training and sport practice.

5. The method of claim 1, wherein the muscle damaging exercise is intense and prolonged.

* * * * *